United States Patent
Matsuzaki

(10) Patent No.: US 11,127,153 B2
(45) Date of Patent: Sep. 21, 2021

(54) RADIATION IMAGING DEVICE, IMAGE PROCESSING METHOD, AND IMAGE PROCESSING PROGRAM

(71) Applicant: HITACHI, LTD., Tokyo (JP)

(72) Inventor: Kazuki Matsuzaki, Tokyo (JP)

(73) Assignee: HITACHI, LTD., Tokyo (JP)

(*) Notice: Subject to any disclaimer, the term of this patent is extended or adjusted under 35 U.S.C. 154(b) by 0 days.

(21) Appl. No.: 16/650,438

(22) PCT Filed: Aug. 8, 2018

(86) PCT No.: PCT/JP2018/029762
§ 371 (c)(1),
(2) Date: Mar. 25, 2020

(87) PCT Pub. No.: WO2019/073681
PCT Pub. Date: Apr. 18, 2019

(65) Prior Publication Data
US 2020/0226779 A1    Jul. 16, 2020

(30) Foreign Application Priority Data
Oct. 10, 2017  (JP) .............................. JP2017-197051

(51) Int. Cl.
| | | |
|---|---|---|
| *G06K 9/00* | (2006.01) | |
| *G06T 7/70* | (2017.01) | |
| *A61B 6/03* | (2006.01) | |
| *A61B 6/12* | (2006.01) | |
| *A61B 6/00* | (2006.01) | |

(Continued)

(52) U.S. Cl.
CPC ................ *G06T 7/70* (2017.01); *A61B 6/022* (2013.01); *A61B 6/032* (2013.01); *A61B 6/12* (2013.01);
(Continued)

(58) Field of Classification Search
CPC .................. G06K 9/4671; G06K 9/685; G06T 2207/20081
See application file for complete search history.

(56) References Cited

U.S. PATENT DOCUMENTS

2005/0251028 A1    11/2005  Boese et al.
2008/0018643 A1*    1/2008  Feilkas ..................... G06T 7/50
                                                   345/420

(Continued)

FOREIGN PATENT DOCUMENTS

JP       2005312962 A    11/2005
JP       2010240253 A    10/2010

(Continued)

OTHER PUBLICATIONS

International Search Report of PCT/JP2018/029762 dated Nov. 6, 2018.

(Continued)

*Primary Examiner* — Hadi Akhavannik
(74) *Attorney, Agent, or Firm* — Mattingly & Malur, PC

(57) ABSTRACT

A radiographic imaging apparatus acquires a plurality of two-dimensional pickup images taken at different angles and a three-dimensional image of a processing target imaged in advance. Two-dimensional calculated projection images are generated from the three-dimensional image, respectively, in association with the two-dimensional pickup images. A characteristic region indicates a treatment instrument represented in the two-dimensional pickup image. The two-dimensional pickup image is aligned with the calculated projection image. A deformation amount of the processing target in the two-dimensional pickup image is calculated by comparing the two-dimensional pickup image with the calculated projection image, and a position of the characteristic region is corrected. A three-dimensional position of the characteristic region is calculated and corrected on the basis (Continued)

of anatomical structure information of the processing target. A position mapping part then superimposes the corrected three-dimensional position of the characteristic region on the three-dimensional image to be displayed on a display unit.

8 Claims, 12 Drawing Sheets

(51) Int. Cl.
   *G06T 5/00* (2006.01)
   *G06T 11/00* (2006.01)
   *A61B 6/02* (2006.01)
   *A61B 1/267* (2006.01)

(52) U.S. Cl.
   CPC ............ *A61B 6/466* (2013.01); *A61B 6/5205* (2013.01); *A61B 6/527* (2013.01); *G06T 5/006* (2013.01); *G06T 11/008* (2013.01); *A61B 1/2676* (2013.01); *G06T 2207/10116* (2013.01); *G06T 2210/41* (2013.01)

(56) References Cited

U.S. PATENT DOCUMENTS

| | | | | |
|---|---|---|---|---|
| 2008/0037843 A1* | 2/2008 | Fu | ............................ | G06T 7/11 382/128 |
| 2014/0016854 A1* | 1/2014 | Nagatomo | .............. | G06T 7/001 382/149 |
| 2014/0371578 A1 | 12/2014 | Auvray et al. | | |
| 2015/0042643 A1 | 2/2015 | Shibata et al. | | |
| 2015/0145966 A1* | 5/2015 | Krieger | ................ | H04N 13/122 348/47 |
| 2015/0276395 A1* | 10/2015 | Kisanuki | ................ | G01B 21/32 702/152 |
| 2016/0148401 A1* | 5/2016 | Hirai | ......................... | G06T 7/30 382/131 |
| 2017/0337682 A1* | 11/2017 | Liao | ........................... | G06T 7/30 |
| 2017/0340311 A1* | 11/2017 | Shiki | ...................... | A61B 8/483 |
| 2018/0070902 A1* | 3/2018 | Lin | ...................... | A61B 5/1077 |

FOREIGN PATENT DOCUMENTS

| | | |
|---|---|---|
| JP | 2011050621 A | 3/2011 |
| JP | 2015503416 A | 2/2015 |
| JP | 5787030 A2 | 9/2015 |

OTHER PUBLICATIONS

International Preliminary Report on Patentability received in corresponding International Application No. PCT/JP2018/029762 dated Apr. 14, 2020.

* cited by examiner

RADIATION IMAGING DEVICE, IMAGE PROCESSING METHOD, AND IMAGE PROCESSING PROGRAM

TECHNICAL FIELD

The present invention relates to a radiographic imaging apparatus, an image processing method, and an image processing program. More particularly, the present invention relates to the radiographic imaging apparatus, the image processing method, and the image processing program configured to acquire a projection image used for performing examination or treatment with inserting a treatment instrument into a subject.

BACKGROUND ART

There is known a radiographic imaging apparatus (hereinafter, simply referred to as "X-ray imaging apparatus") having an X-ray source and a two-dimensional X-ray detector installed facing each other, configured to take a static image or a moving image of a subject, with the fixed or moving X-ray source and the two-dimensional X-ray detector. There are also known techniques that use a projection X-ray image taken by the X-ray imaging apparatus, when examination or treatment is performed with inserting a treatment instrument such as an endoscope and a catheter into a body of a subject. This technique has an advantage that the examination or treatment can be conducted along with ensuring a position or a direction of the treatment instrument in the projection X-ray image in real time.

For example, this projection X-ray image is also used in carrying out so-called "biopsy" to perform an examination for a confirmed diagnosis of lung cancer, that is, collection of a sample with the use of a bronchoscope. To perform this examination, a guide-sheath is inserted toward peripheral lung fields under the bronchoscope. In the case of a bronchus of peripheral lung, in particular, into which the bronchoscope cannot be inserted, the guide-sheath is guided and maintained at peripheral pulmonary lesions, along with ensuring the position and direction of the treatment instrument with reference to the projection X-ray image. Then, via the guide-sheath, a biopsy forceps or a cytology brush is made to reach the lesions, so as to take a sample. In performing the biopsy using the projection X-ray image as described above, a sample has to be taken from the lesions, and thus, it is necessary for an operator to figure out a positional relationship between an affected area being the lesions and the treatment instrument, with extremely high accuracy.

Though the operator can figure out the position of the treatment instrument such as the biopsy forceps and the cytology brush in the projection X-ray image, it is not possible for the operator to accurately determine the position in the projecting direction, because the projection X-ray image is a two-dimensional image. In other words, when an axis connecting the X-ray tube and the detector (the center) of the X-ray imaging apparatus is considered, the operator is able to identify the position and the direction of the treatment instrument easily in the direction perpendicular to the axis in the projection X-ray image. On the other hand, it is difficult to accurately identify the position and the direction of the treatment instrument in the direction parallel to the axis (depth direction), because the depth direction corresponds to the projecting direction. In other words, even though the lesions and the treatment instrument appear to be superimposed one on another in the projection X-ray image (represented as such on the image), the treatment instrument does not necessarily reach the lesions.

A difference in absorption of X-rays passing through internal body substances is shown in the form of image, in the projection X-ray image. Therefore, typically, substances such as bones with a high absorption rate are easily represented in the image, whereas representation of substances such as soft tissue with a low absorption rate is difficult. In other words, in the projection X-ray image, images of bones and other similar substances may be high in contrast, but soft tissue including a tumor and the like, may be low in contrast, and thus identifying such lesions in the soft tissue is not easy. It is also difficult to identify in the projection X-ray image, a type of lung cancer, referred to as Ground Glass Opacity (GGO). Due to the same reason, blood vessels and bronchus through which a treatment instrument is made pass, are hard to be identified in the projection X-ray image. As discussed above, a lesion area in an X-ray radiographic image is low in visibility in the first place, and it is further difficult to figure out the positional relationship between the lesion area and the treatment instrument, and between blood vessels or bronchus and the treatment instrument.

In order to increase visibility of the treatment instrument in each image, the Patent Literature 1 discloses a medical X-ray apparatus configured to superimpose a stereoscopic image based on a three-dimensional image on a projection X-ray image obtained by an X-ray imager, and to display a position of an object. More specifically, in the medical X-ray apparatus as described in the Patent Literature 1, a three-dimensional image taken in advance and an X-ray radiographic image acquired during an examination are used to detect a three-dimensional position of a treatment instrument, and body motion of a subject is considered as a constant shift with respect to thus detected three-dimensional position, whereby the three-dimensional position of the treatment instrument is corrected to detect the position thereof.

CITATION LIST

Patent Literature

Patent Literature 1
Japanese Patent No. 5787030

DISCLOSURE OF THE INVENTION

Problems to be Solved by the Invention

During the examination such as the biopsy using the bronchoscope, in particular, movements including body motion of the subject are liable to be a problem. Such body motion of the subject includes, for example, respiratory movement of lungs and beating movement around the heart. Since lungs have a complex structure including a trachea, bronchus, and alveolus, and further lungs have a structure of soft tissue, complex movements tend to be caused by a lesion, blood vessels, and insertion of a treatment instrument. Therefore, it is essential to figure out a three-dimensional position in view of such complex movements.

However, the medical X-ray apparatus as disclosed by Patent Literature 1 considers the body motion of the subject as a constant shift, and the three-dimensional position of the treatment instrument is corrected only based on this constant shift. Therefore, this configuration cannot correct deformation (shift) caused by the aforementioned complex movement of the trachea, bronchus, alveolus, and so on, or caused by inserting the treatment instrument. In other words, the medical X-ray apparatus as disclosed by Patent Literature 1 only regards the respiratory movement mainly as body motion of the subject. Even as for the respiration, variations in tissue and structure within a body caused by respiration are assumed to be ignorable in a region of interest, and thus the amount of variation is considered as constant. In other words, in Patent Literature 1, the motion of the subject caused by respiration is regarded as a constant amount, and further, complex motions other than the respiration is not considered at all.

In particular, deformation due to the insertion of the treatment instrument as described above should cause a shape different from the shape of the bronchus in the three-dimensional image taken in advance. Thus, it is anticipated that there should be displacement from the three-dimensional position of the treatment instrument, which has been identified in the projection X-ray image. Accordingly, it is difficult to figure out an accurate position of the treatment instrument, only by correcting the shift based on the body motion caused by respiration.

The present invention has been made in view of the situation above, and an objective of the present invention is to detect an accurate three-dimensional position of a treatment instrument, and to display the position in the image with a high degree of precision.

Means for Solving the Problems

In order to solve the problems, the present invention provides the following means. According to the present invention, there is provided a radiographic imaging apparatus comprising, an imager configured to take a plurality of two-dimensional pickup images at different imaging angles by moving positions of a radiation source and a detector, an image capturing part configured to acquire a three-dimensional image of a processing target imaged in advance, a calculated projection image generator configured to generate two-dimensional calculated projection images from the three-dimensional image, respectively in association with the two-dimensional pickup images, on the basis of the three-dimensional image and the positions of the radiation source and the detector used for taking each of the two-dimensional pickup images, a characteristic region extractor configured to extract a characteristic region indicating a treatment instrument represented in each of the two-dimensional pickup images, an image alignment part configured to align each of the two-dimensional pickup images with each of the calculated projection images respectively associated with the two-dimensional pickup images, a deformation amount calculation and correction part configured to calculate a deformation amount of the processing target in the two-dimensional pickup image, by comparing each of the two-dimensional pickup images with each of the calculated projection images respectively associated with the two-dimensional pickup images, and to correct a position of the characteristic region based on the deformation amount, a three-dimensional position calculator configured to calculate a three-dimensional position of the characteristic region, from the position of the characteristic region corrected in each of the two-dimensional pickup images and the positions of the radiation source and the detector used for taking each of the two-dimensional pickup images, an anatomical structure position correction part configured to correct the three-dimensional position of the characteristic region based on anatomical structure information of the processing target acquired from the three-dimensional image, and a position mapping part configured to superimpose the three-dimensional position of the characteristic region corrected by the anatomical structure correction part, on the three-dimensional image, and to display the three-dimensional image on which thus corrected three-dimensional position of the characteristic region is superimposed.

Advantage of the Invention

According to the present invention, a three-dimensional position of the treatment instrument can be detected accurately, and displayed in the image with a high degree of precision.

BEST MODE FOR CARRYING OUT THE INVENTION

Figure 1:
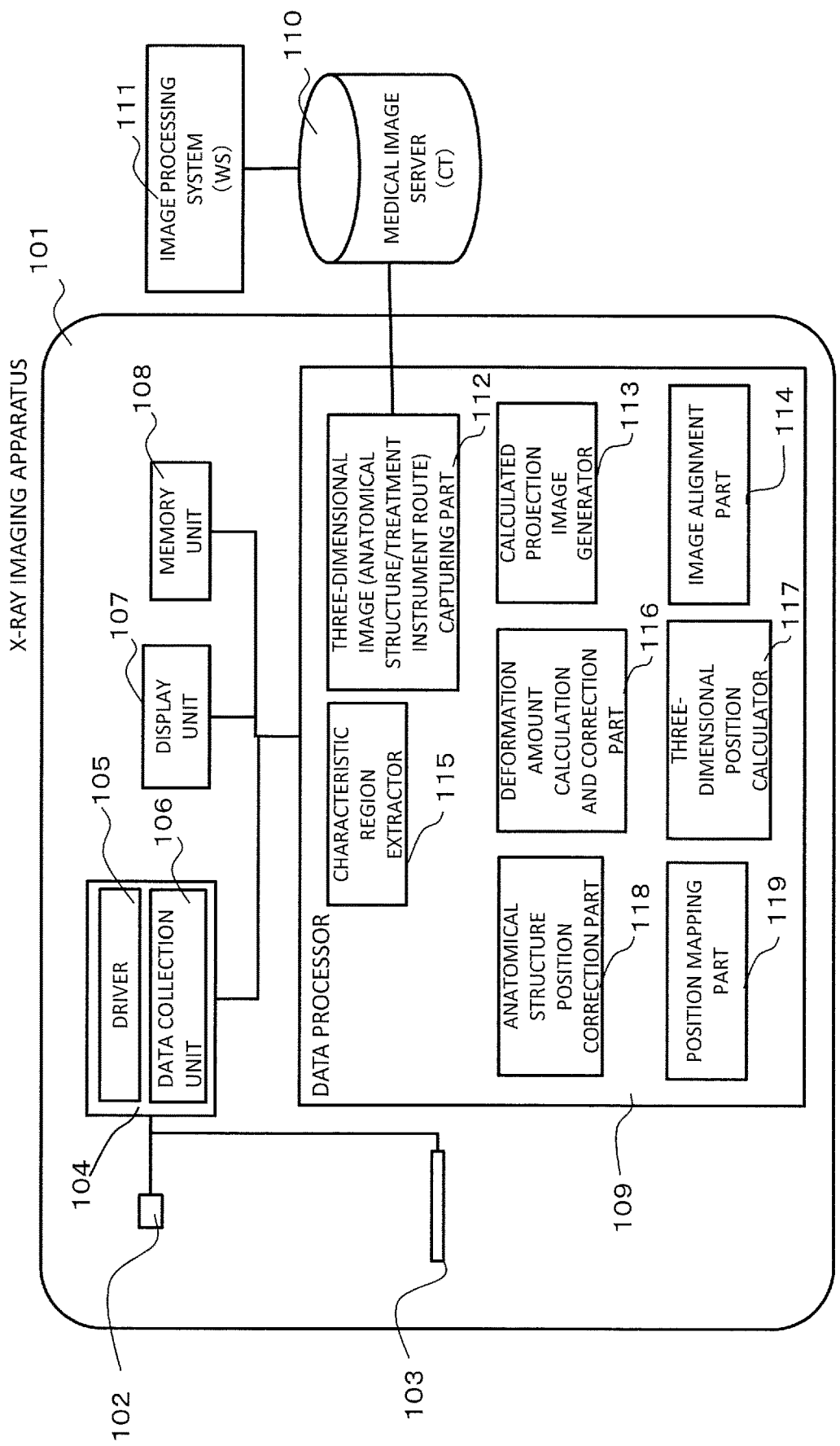
FIG. 1 is a block diagram showing a schematic configuration of an X-ray imaging apparatus according to an embodiment of the present invention.

A radiographic imaging apparatus according to an embodiment of the present invention comprises, an imager configured to take a plurality of two-dimensional pickup images at different imaging angles by moving positions of a radiation source and a detector, an image capturing part configured to acquire a three-dimensional image of a processing target imaged in advance, a calculated projection image generator configured to generate two-dimensional calculated projection images from the three-dimensional image, respectively in association with each of the two-dimensional pickup images, on the basis of the three-dimensional image and the positions of the radiation source and the detector used for taking each of the two-dimensional pickup images, a characteristic region extractor configured to extract a characteristic region indicating a treatment instrument represented in each of the two-dimensional pickup images, an image alignment part configured to align each of the two-dimensional pickup images with each of the calculated projection images respectively associated with the two-dimensional pickup images, a deformation amount calculation and correction part configured to calculate a deformation amount of the processing target in the two-dimensional pickup image, by comparing each of the two-dimensional pickup images with each of the calculated projection images respectively associated with the two-dimensional pickup images, and to correct a position of the characteristic region based on the deformation amount, a three-dimensional position calculator configured to calculate a three-dimensional position of the characteristic region, from the position of the characteristic region corrected in each of the two-dimensional pickup images and the positions of the radiation source and the detector used for taking each of the two-dimensional pickup images, an anatomical structure position correction part configured to correct the three-dimensional position of the characteristic region based on anatomical structure information of the processing target acquired from the three-dimensional image, and a position mapping part configured to superimpose the three-dimensional position of the characteristic region corrected by the anatomical structure correction part, on the three-dimensional image, and to display the three-dimensional image on which thus corrected three-dimensional position of the characteristic region is superimposed.

There will now be described an embodiment of the present invention more in detail, with reference to the accompanying drawings. In the present embodiment, an example will be described where an X-ray imaging apparatus is used as one embodiment of a radiographic imaging apparatus. With reference to the drawings, the X-ray imaging apparatus according to the present embodiment will be described. The X-ray imaging apparatus of the present embodiment is just one example of radiographic imaging apparatuses, and the present embodiment is applicable to any radiographic imaging apparatus that acquires an image, using not only X-rays but also others.

As illustrated in FIG. 1, the X-ray imaging apparatus 101 is connected directly with a medical image server 110 via wired or wireless network, communicating each other. In the present embodiment, the medical image server 110 may store, for example, various medical images such as a CT image, an MRI image, and a PET image or an ultrasound image. Such communication and storage of images and information via the network are implementable by using DICOM format that is commonly used in a medical field. In addition, the medical image server 110 is connected to an external image processing system 111, and the medical image server is capable of storing images and information that are results of processing in the image processing system 111, and delivering thus stored images and information to the X-ray imaging apparatus 101.

The X-ray imaging apparatus 101 is provided with an X-ray source 102, a detector 103, a device controller 104, a display unit 107, a memory unit 108, and a data processor 109. The detector 103 detects X-rays applied from the X-ray source 102 and passed through the subject. The device controller 104 is provided with a driver 105 for driving the X-ray source 102 and the detector 103, and a data collection unit 106 for collecting data detected by the detector 103. The display unit 107 displays results collected by the data collection unit 106 and processed by the data processor 109. The memory unit 108 stores various data collected by the data collection unit 106, and results and others processed by the data processor 109.

The data processor 109 is provided with a three-dimensional image capturing part 112, a calculated projection image generator 113, an image alignment part 114, a characteristic region extractor 115, a deformation amount calculation and correction part 116, a three-dimensional position calculator 117, an anatomical structure position correction part 118, and a mapping part 119.

The three-dimensional image capturing part 112 acquires a given three-dimensional image from the medical image server 110, and also acquires anatomical structure information. The three-dimensional image may be, for example, an image that is used in advance for diagnosing a lesion area and for planning a route or the like, for inserting a treatment instrument to reach the lesion area. Typically, images such as a CT image, an MRI image, and a PET image can be used as the three-dimensional image. In addition, any three-dimensional image may be used, suitable for diagnosis and examination of the lesion area. In the following, a CT image is described as the three-dimensional image, by way of example. In the present embodiment, the anatomical structure information indicates information representing a structure of organs and others within a subject, including a bronchial structure such as a bronchial tree. This is information obtainable from the three-dimensional image.

The calculated projection image generator 113 generates a two-dimensional calculated projection image, on the basis of the three-dimensional image acquired by the three-dimensional image capturing part 112. More specifically, the calculated projection image generator 113 uses the three-dimensional image acquired by the three-dimensional image capturing part 112 to calculate the two-dimensional calculated projection image on the basis of the positions of the X-ray source 102 and the detector 103.

Figure 2:
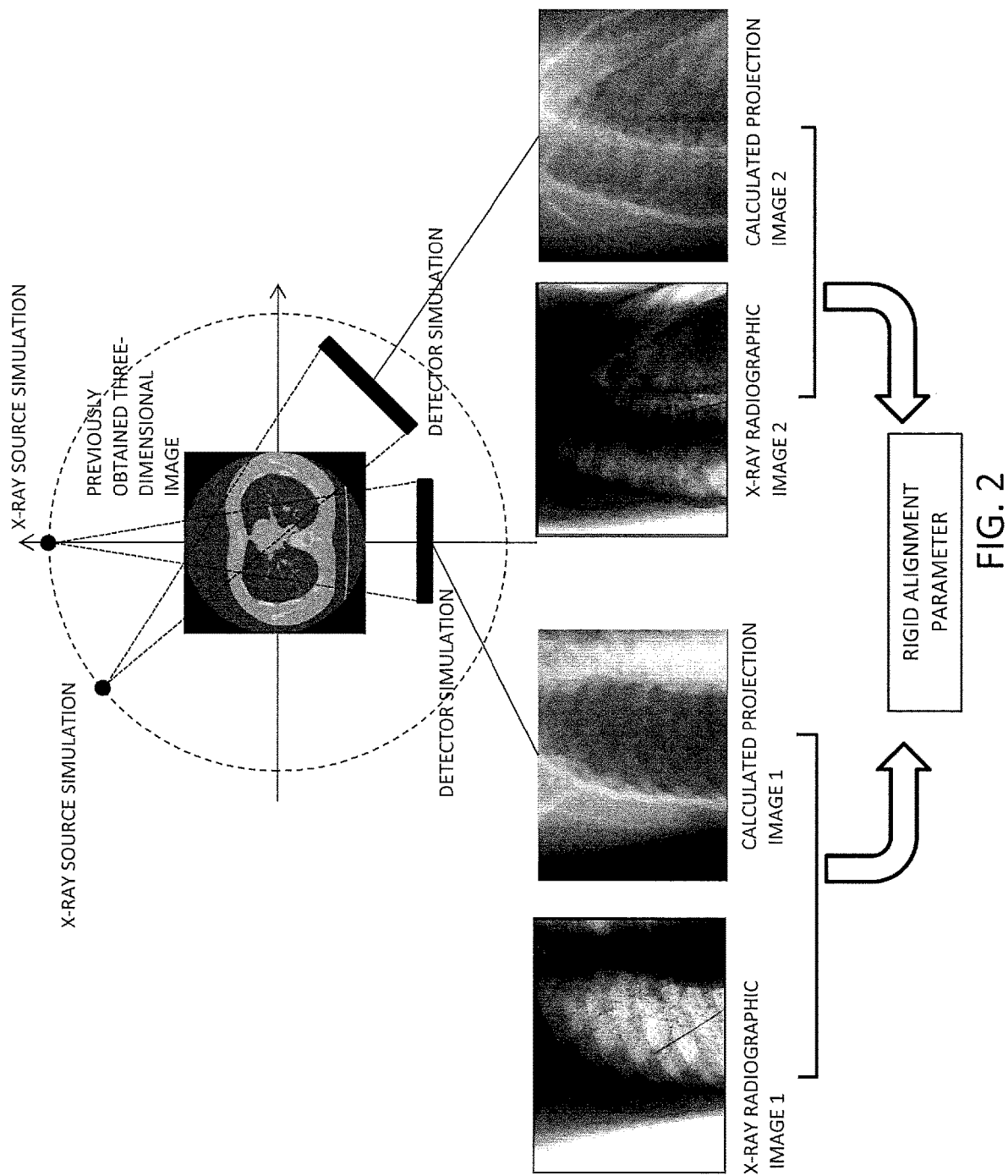
FIG. 2 illustrates one example of a simulation system where a three-dimensional image, an X-ray source, and a detector are arranged under simulated usage conditions, in the X-ray imaging apparatus according to an embodiment of the present invention.

The calculated projection image in this embodiment corresponds to an image that is obtained by projecting simulated X-rays (RAY) from the X-ray source 101 to the detector 102, and by calculating (ray tracing) a detected image (e.g., passage distance, pixel values, and so on) based on the simulated X-rays in the detector 102, in a simulation system where the three-dimensional image acquired by the three-dimensional image capturing part 112 is placed as shown in FIG. 2, in a spatial arrangement of the X-ray source 102 and the detector 103 in the X-ray imaging apparatus 101. The calculated projection image is also referred to as DRR (Digital Reconstructed Radiograph) image, for instance.

Three-dimensional positions of the X-ray source 102 and the detector 103 when the X-ray radiographic image was acquired can be determined according to the configuration of the X-ray imaging apparatus, and an imaging angle of the X-ray radiographic image is already known. Therefore, considering the alignment as described later, the calculated projection image is calculated with the arrangement simulating the positional relationship between the X-ray source 102, detector 103, and their rotation angle. For example, the ray tracing method as described above is employed, to calculate the calculated projection image as a numerical value obtained by adding in the ray direction, pixel values of an image as the three-dimensional image. In addition, the calculated projection image is calculated at every angle when the X-ray radiographic image is acquired.

First, the image alignment part 114 aligns the X-ray radiographic image with the calculated projection image. That is, the image alignment part 114 performs alignment of the two-dimensional X-ray radiographic image acquired by the X-ray imaging apparatus 101, with the calculated projection image generated by the calculated projection image generator 113 (see FIG. 2).

Since these two images are two-dimensional images, the image alignment part 114 moves and rotates the calculated projection image, and calculates a degree of similarity between the calculated projection image and the X-ray radiographic image (e.g., an amount of mutual information). Then, a movement and rotation parameter that maximizes or minimizes a value indicating the degree of similarity is obtained as a rigid alignment parameter. Besides the degree of similarity, the movement and rotation parameter allowing a reference portion of one image to associate with that of the other image may also be calculated, and used as the rigid alignment parameter.

The image alignment part 114 calculates, for example, as the rigid alignment parameter for the alignment, translation 3 degrees of freedom and rotation (rotation within a plane) 2 degrees of freedom about an axis along the imaging direction, according to the alignment between the calculated projection image generated from the three-dimensional image, and the X-ray radiographic image. By using thus calculated parameters, the X-ray radiographic image is aligned with the calculated projection image.

This calculation of the rigid alignment parameters for aligning the three-dimensional image and the two-dimensional image may be performed by a method different from the aforementioned method where the calculated projection image is obtained from the three-dimensional image and aligned with the X-ray radiographic image. For example, the three-dimensional image is moved and rotated to generate the calculated projection image, and comparison of pixel values between the calculated projection image and the X-ray radiographic image is repeated. Then, searching for a parameter that maximizes or minimizes the degree of similarity allows obtainment of translation (orthogonal axis) 3 degrees of freedom and rotation 3 degrees of freedom around each of the orthogonal axes, i.e., 6 degrees of freedom in total.

Any alignment method may be used for aligning the images in the present embodiment, and various methods are applicable. This alignment is so-called rigid alignment that performs alignment of six parameters of movement and rotation in the three-dimensional image. Therefore, it is suitable for alignment of rigid area such as bones.

The characteristic region extractor 115 extracts as a characteristic region, one or more characteristic areas indicating an instrument such as a treatment instrument in the X-ray radiographic image. It is possible to use as the characteristic region, an area indicating a marker provided on the treatment instrument, or the tip of the treatment instrument, for instance.

Figure 3:
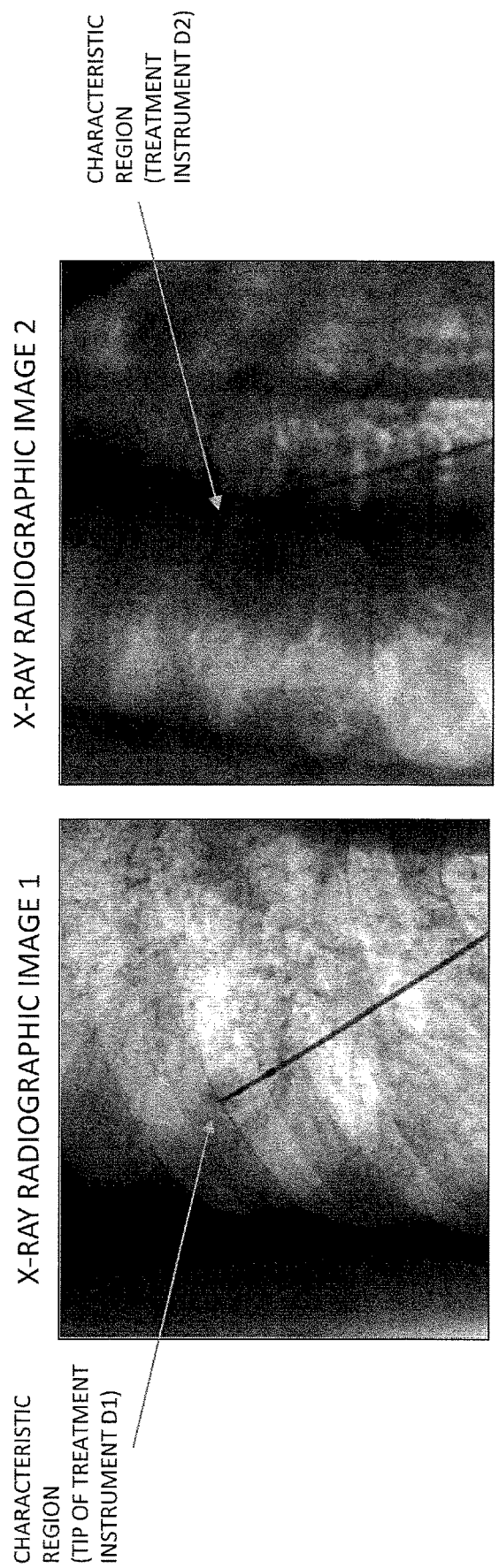
FIG. 3 shows references indicating one example of the X-ray radiographic image taken in the state where a treatment instrument is inserted into a subject, in the X-ray imaging apparatus according to an embodiment of the present invention.

FIG. 3 shows examples of the X-ray radiographic image taken in the state that the treatment instrument was inserted in the subject. As shown in FIG. 3, the area of the treatment instrument has a high X-ray absorption rate. Therefore, as shown in FIG. 3, the treatment instrument has high contrast relative to human body structure in the X-ray radiographic image. On the basis of a contrast difference between the area indicating the human body structure and the area indicating the treatment instrument in the X-ray radiographic image, an area with high contrast is extracted, and thereby the tip of forceps being the treatment instrument is detected as the characteristic region, for instance.

In addition, in the case where the treatment instrument is a guide-sheath, the marker provided on the guide-sheath is extracted as a region indicating brightness different from the brightness of the human body structure or of the guide-sheath main body, in the X-ray radiographic image. Therefore, the marker can be extracted as the characteristic region of the treatment instrument.

The deformation amount calculation and correction part 116 calculates a deformation amount of the subject, from the X-ray radiographic image and the calculated projection image, and corrects the position of the characteristic region within the imaging plane, the position having been extracted by the characteristic region extractor 115. The X-ray radiographic image acquired by the X-ray imaging apparatus and the three-dimensional image obtained in advance were taken by different devices. Therefore, it is a matter of course that those images were not taken at the same point of time, and generally, posture, circumstances, and other situations were different. Furthermore, a human body is liable to be deformed non-rigidly due to body motion of the subject, such as cardiac motion and respiration. In many cases, deformation due to such body motion as described above is apt to be included in two or more images taken at different points of imaging time.

In the case where the treatment instrument is inserted into the body, the insertion may cause deformation in the internal body tissue, since the internal-body soft tissue area is typically softer than the treatment instrument. Such deformation may rarely occur in a firm area such as bones, so-called rigid area, but deformation is liable to occur in a soft area such as a soft tissue area. In addition, the instrument such as the treatment instrument may be inserted into a tubular tissue, and thus influence of body motion is inevitable along with the soft tissue. Therefore, when the treatment instrument is inserted into the body, deformation due to the treatment instrument may be included in the X-ray radiographic image and between the X-ray radiographic images.

In other words, deformation that occurs in the subject may include, broadly, two types of deformation; deformation due to body motion such as cardiac motion and respiration, and deformation due to insertion of the treatment instrument into the body. Therefore, the deformation amount calculation and correction part 116 corrects these two types of deformation as appropriate.

Figure 4:
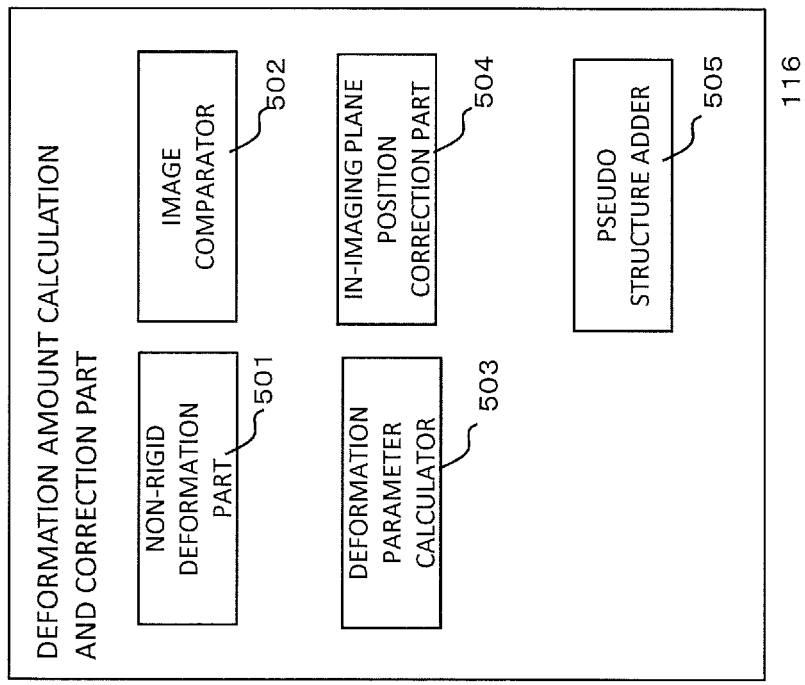
FIG. 4 is a block diagram showing a schematic configuration of a deformation amount calculation and correction part, in the X-ray imaging apparatus according to an embodiment of the present invention.

As shown in FIG. 4, in order to correct such deformation, the deformation amount calculation and correction part 116 is provided with a non-rigid deformation part 501, an image comparator 502, a deformation parameter calculator 503, an in-imaging plane position correction part 504, and a pseudo structure adder 505.

Figure 5:
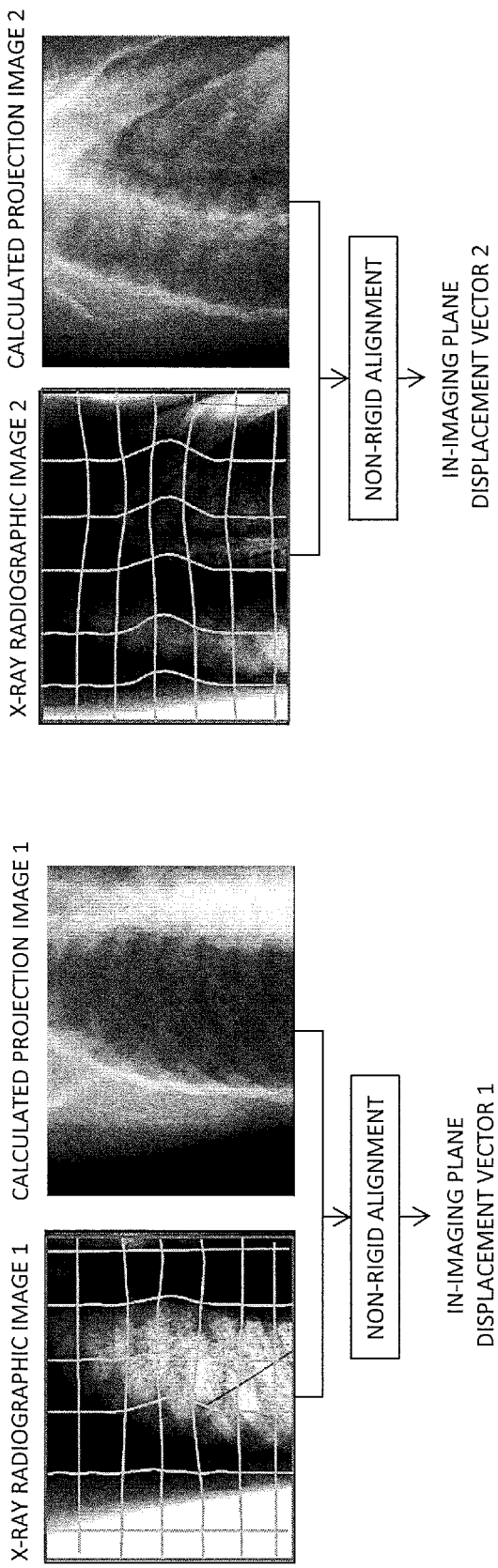
FIG. 5 illustrates non-rigid deformation performed by the deformation amount calculation and correction part, in the X-ray imaging apparatus according to an embodiment of the present invention.

The non-rigid deformation part 501 performs non-rigid deformation of the X-ray radiographic image. More in detail, as shown in FIG. 5, the non-rigid deformation part 501 provides a lattice-pattern mesh on the X-ray radiographic image, and moves each of points on the lattice pattern, assuming that the points move along a smooth curve such as a spline function, for example. Then, the non-rigid deformation part 501 transforms pixels in response to the movement of each of the lattice-like points, thereby performing non-rigid deformation. Selection of one or more of the moving lattice points, the amount of movement, and the direction of movement may be predetermined as appropriate.

The image comparator 502 compares the X-ray radiographic image subjected to the non-rigidity transform by the non-rigid deformation part 501, with the calculated projection image, and calculates a degree of similarity therebetween. As in the case of the degree of similarity calculation in the image alignment part 114, both the two images are two-dimensional images. Therefore, the calculated projection image is moved and rotated, so as to calculate the degree of similarity (e.g., mutual information amount) between the X-ray radiographic image after the non-rigid deformation, and the calculated projection image with attenuated rigid area.

The deformation parameter calculator 503 calculates as a non-rigid deformation parameter, a parameter that maximizes a value indicating the degree of similarity (or minimizes the value indicating a degree of difference), among the degrees of similarity calculated by the image comparator 502.

The in-imaging plane position correction part 504 calculates a deformation displacement representing to what extent the position of the characteristic region has moved in the two-dimensional image on the basis of the non-rigid deformation parameter, and corrects the position of the characteristic region within the plane of the X-ray radiographic image. A displacement vector calculated as the deformation displacement can be obtained from the position of the characteristic region before the non-rigid alignment and the position of the characteristic region after the non-rigid alignment. It is also possible to calculate a vector connecting the position before the alignment with the position after the alignment.

Figure 6:
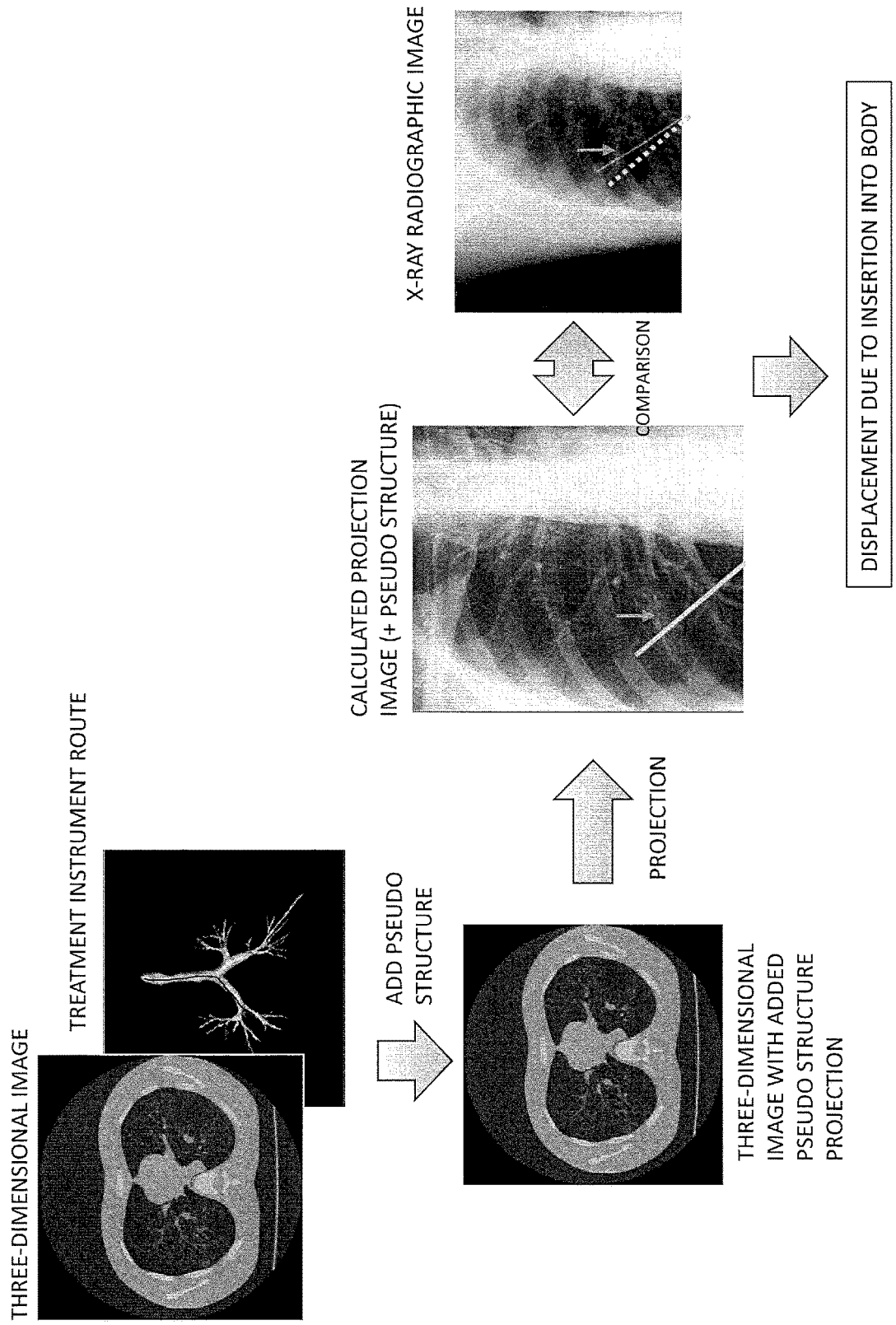
FIG. 6 illustrates addition of a pseudo structure by a pseudo structure adder, in the X-ray imaging apparatus according to an embodiment of the present invention.

The pseudo structure adder 505 acquires shapes based on the internal body structure of the subject, for example, trachea and bronchus, and an insertion route of the treatment instrument, calculated in advance by the image processing system 111 and stored in the medial data server 110, together with the three-dimensional image acquired by the three-dimensional image capturing part 112, and then adds thus obtained route of the treatment instrument as a pseudo structure to the three-dimensional image as shown in FIG. 6.

Since the internal body structure is clear in the three-dimensional image, it is easy to figure out the tubular structure including trachea and bronchus. Therefore, generation of tracheal and bronchial data, and the insertion route of the treatment instrument to reach a lesion area are planned in advance, and the treatment instrument route along the trachea and bronchus can be generated and stored as data in the form of a group of points or a group of lines. Thus, storing in advance such data as described above in a storage device such as the medical image server 110 allows easy acquisition of the route of the treatment instrument.

In the upper left of FIG. 6, there is shown an example of data regarding the three-dimensional image and the treatment instrument route acquired from the medical image server 110. That is, the pseudo structure adder 505 adds to and superimposes on the three-dimensional image, the information regarding the treatment instrument route in the form of pseudo structure. Then, comparing the calculated projection image with the X-ray projected image allows comparison between the position of the pseudo structure in the calculated projection image, and the actual position of the characteristic region (the position of the treatment instrument). According to the displacement between the positions of the pseudo structure and the characteristic region, it is possible to figure out whether or not deformation has occurred in the subject due to the insertion of the treatment instrument.

The three-dimensional position calculator 117 calculates a three-dimensional position of the characteristic region, on the basis of the position of the X-ray source and the position of the characteristic region identified in the X-ray radiographic image. Specifically, for example, the tip position of the treatment instrument being the characteristic region extracted in the X-ray radiographic image, and the position of the detector 103 associated with the tip position of the treatment instrument are obtained. The three-dimensional position on the associated detector 103 can be obtained from the device configuration of the detector 103 in the X-ray imaging apparatus 101. This is because the tip position of the treatment instrument in the X-ray radiographic image is an image projected from the X-ray source to the detector 103, and thus the tip of the treatment instrument should be located at a three-dimensional position on the line connecting the X-ray source with the tip of the treatment instrument in the X-ray radiographic image. As a result, the three-dimensional position calculator 113 can calculate, for example, three-dimensional positions (D1 and D2 in FIG. 7) of thus extracted tip position of the forceps on the detector 103 (in the X-ray radiographic image).

Furthermore, in the case where there is a plurality of characteristic regions on the treatment instrument, the three-dimensional position calculator 117 calculates as to each of the characteristic regions, a line connecting two points, i.e., the three-dimensional position on the detector 103 (in the X-ray radiographic image) and the three-dimensional position of the X-ray source. The three-dimensional position of the X-ray source 102 can be obtained from the device configuration of the X-ray source 102 of the X-ray imaging apparatus 101. Therefore, it is possible to calculate a line connecting two points, i.e., the three-dimensional position of the forceps tip as the characteristic region, for example, on the detector 103 (in the two-dimensional X-ray radiographic image), and the three-dimensional position of the X-ray source 102.

In the X-ray imaging apparatus, more than one imaging is performed at different angles with respect to the subject, and thus there are acquired a plurality of X-ray radiographic images. Therefore, for example, as to the X-ray radiographic images taken at different two angles, the three-dimensional position calculator 117 can obtain two lines for each characteristic region, the line connecting the three-dimensional position of the X-ray source, with the three-dimensional position on the detector 103 (in the X-ray radiographic image) of the characteristic regions such as the tip of forceps tip and a marker of guide-sheath. The three-dimensional position calculator 117 uses a positional relationship between two lines calculated regarding each characteristic region of the treatment instrument in a plurality of X-ray radiographic images taken at different angles, so as to calculate a three-dimensional position of the characteristic region indicating the treatment instrument.

Figure 7:
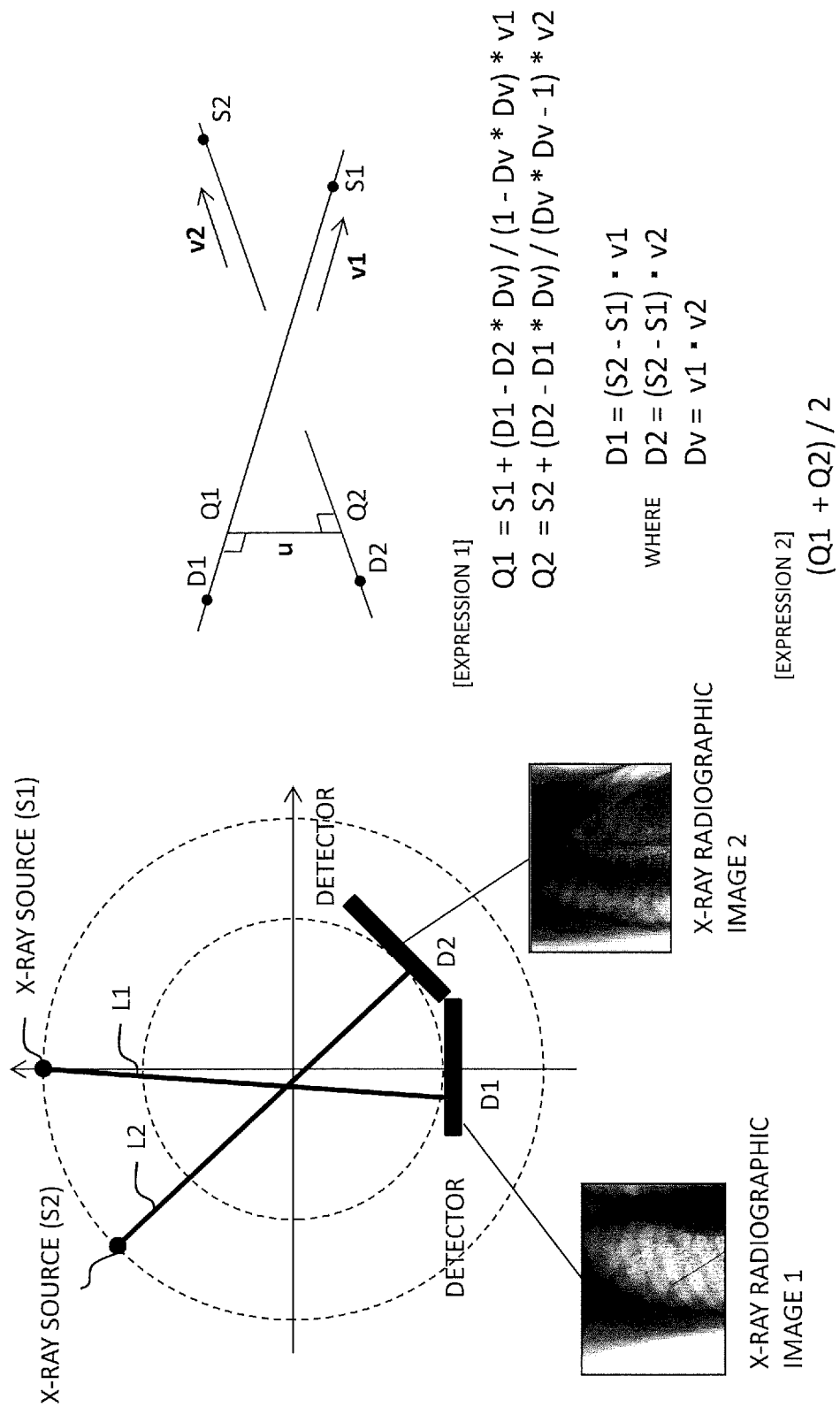
FIG. 7 illustrates one example of a processing for calculating a three-dimensional position of the treatment instrument, in the X-ray imaging apparatus according to an embodiment of the present invention.

There will now be described an example for calculating a three-dimensional position of the treatment instrument according to an embodiment of the X-ray imaging apparatus. As shown in FIG. 7, Line L1 connecting the three-dimensional position S1 of the X-ray source, with the three-dimensional position D1 of the characteristic region in the X-ray radiographic image 1, and Line L2 connecting the three-dimensional position S2 of the X-ray source being rotated, with the three-dimensional position D2 of the characteristic region in the X-ray radiographic image 2, are both projection of an identical characteristic region such as the tip of forceps. Therefore, ideally, Lines L1 and L2 should cross at one point, but in actuality, they do not necessarily cross at one point due to errors in measurement, for instance. Under these circumstances, Point Q1 on Line S1-D1 and Point Q2 on Line S2-D2 are obtained, where distance between the two lines becomes the shortest, and for example, the midpoint between the two points can be determined as the forceps tip position.

Points Q1 and Q2 as shown in FIG. 7 can be obtained according to the following expressions:

$$Q1 = S1 + (D1 - D2 \cdot Dv)/(1 - Dv \cdot Dv)v1$$

$$Q2 = S2 + (D2 - D1 \cdot Dv)/(Dv \cdot Dv - 1)v2$$

where $$D1 = (S2 - S1)v1$$

$$D2 = (S2 - S1)v2$$

$$Dv = v1 \cdot v2$$

The three-dimensional position of the forceps tip position can be calculated, from the three-dimensional positions of Points Q1 and Q2 obtained from the expressions described above, by using the following expression:

$$(Q1 + Q2)/2$$

The anatomical structure position correction part 118 corrects the three-dimensional position of the characteristic region calculated by the three-dimensional position calculator 117, on the basis of anatomical structure information of the subject. Correction by the anatomical structure position correction part 118 is performed on the three-dimensional position of the characteristic region as the following.

The three-dimensional images stored in the medical image server 110 include all of three-dimensional structures of the subject. Therefore, a bronchial structure into which an endoscope or a treatment instrument is to be inserted, for example, can be obtained from the three-dimensional images, as anatomical structure information. In the present embodiment, the anatomical structure information obtained from the three-dimensional image is stored in advance in the medical image server 110, in association with the three-dimensional image, and the three-dimensional image capturing part 112 acquires the anatomical structure information from the medical image server 110, together with the three-dimensional image.

Figure 8:
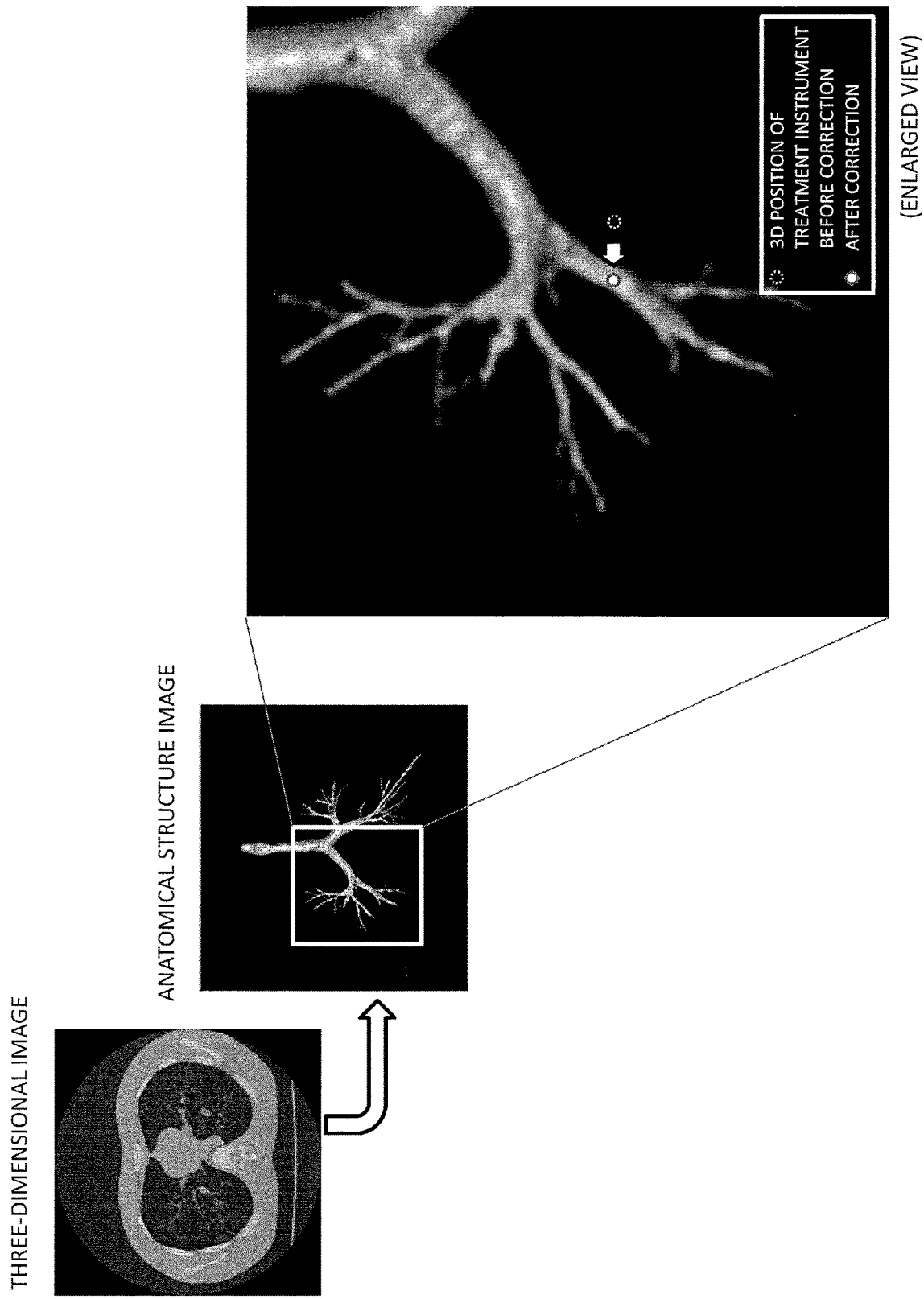
FIG. 8 illustrates one example of a processing for correcting the three-dimensional position of the treatment instrument by the use of anatomical structure information, in the X-ray imaging apparatus according to an embodiment of the present invention.

FIG. 8 shows an example as a result of volume rendering of information related to a bronchial tree as anatomical structure information that is obtained from the three-dimensional image. There will now be described an example where a treatment instrument is inserted into a bronchus. In the case of FIG. 8, the treatment instrument is inserted into the bronchus, and thus the characteristic region indicating the treatment instrument should be within the anatomical structure, that is, within the bronchus. On the basis of this fact, the three-dimensional position of the characteristic region being the treatment instrument is corrected so that the treatment instrument is located within the anatomical structure. More specifically, for example, correction can be made in such a manner that distance between the bronchial structure being anatomical structure information acquired in advance, and the three-dimensional position of the characteristic region indicating the treatment instrument is calculated, and the three-dimensional position of the characteristic region is moved to be located at the shortest distance from the bronchial structure, whereby the three-dimensional position can be corrected to be positioned within the anatomical structure.

The position mapping part 119 adds to, i.e., superimposes on the three-dimensional image acquired by the three-dimensional image capturing part 111, the three-dimensional position of the characteristic region corrected by the anatomical structure position correction part 118. The position of the subject in the X-ray radiographic image, and the position of the subject in the three-dimensional image acquired from the medical image server 110 are aligned by the image alignment part 114.

Therefore, for example, the three-dimensional position of the tip of the treatment instrument as the characteristic region in the X-ray radiographic image can be superimposed on the three-dimensional image. Similarly, in the case where the characteristic region is a marker of guide-sheath, the three-dimensional position of the marker can be superimposed on the three-dimensional image. The position mapping part 119 delivers the three-dimensional image on which the characteristic region is superimposed, to the display unit 107 and to the memory unit 108. Then, for example, as shown in FIG. 9, the three-dimensional image is displayed on the display unit 107 and stored in the memory unit 108.

Figure 9:
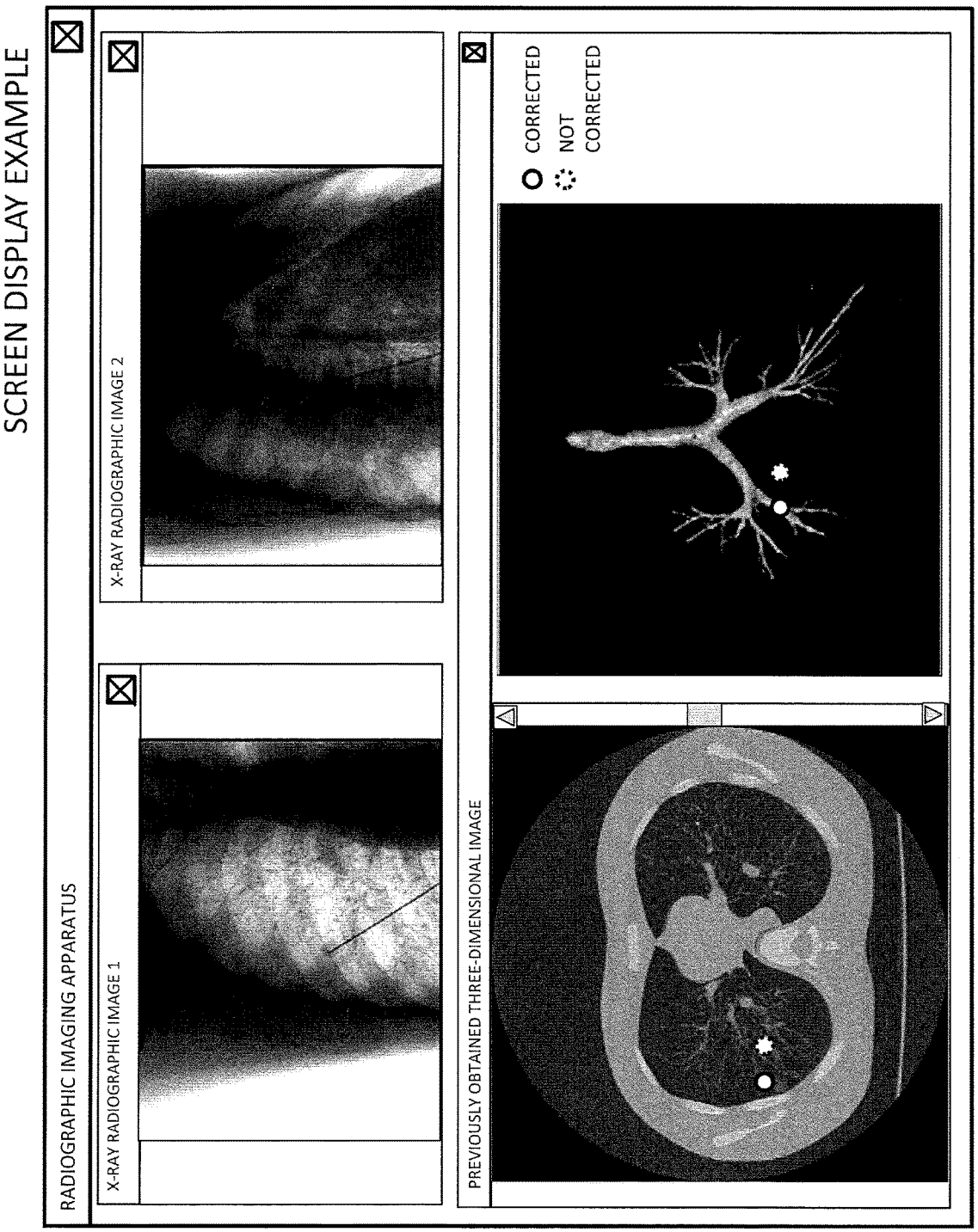
FIG. 9 shows references indicating one example of display screens where a detected position of the treatment instrument is superimposed on the three-dimensional image and the superimposed image is displayed, in the X-ray imaging apparatus according to an embodiment of the present invention.

In the example of FIG. 9, the three-dimensional image is shown in the form of tomographic image, but this three-dimensional image can be shown in another type of image such as a two-dimensional image and a stereoscopic image. In the example in FIG. 9, in addition to the two X-ray radiographic images 1 and 2, mutually different in imaging direction, there are shown an image where the position of the characteristic region (treatment instrument) is superimposed on the three-dimensional image acquired from the medical image server 110, and an image where a three-dimensional image of the characteristic region (treatment instrument) is superimposed on the volume rendering image of the anatomical structure. There are shown on the three-dimensional image and on the volume-rendering image, whether correction was made for the amount of deformation.

Figure 10:
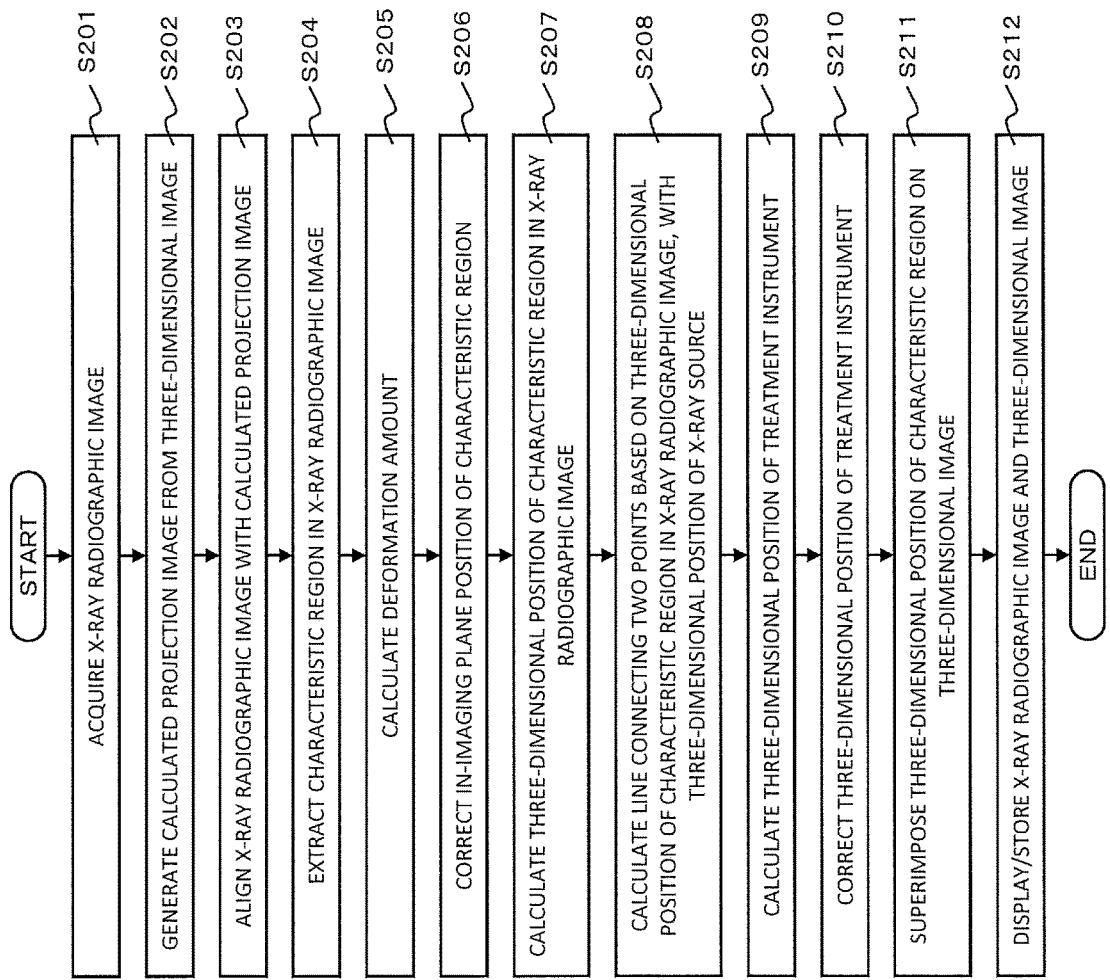
FIG. 10 is a flowchart showing the processing that relates to displaying of an image where the three-dimensional position of the treatment instrument or the like, is represented, in the X-ray imaging apparatus according to an embodiment of the present invention.

With reference to the flowchart of FIG. 10, there will be described a processing for displaying an image representing the three-dimensional position of the treatment instrument or the like, in the X-ray imaging apparatus configured as described above. As for the X-ray radiographic image, more than one X-ray radiographic images taken at different imaging angles is required. However, for the sake of explanatory convenience, there will be described the case where two X-ray radiographic images are acquired.

In step S201, the X-ray imaging apparatus 101 acquires two X-ray radiographic images. In the X-ray imaging apparatus 101, the driver 105 of the drive controller 104 drives the X-ray source 102 and the detector 103 to move them to desired positions, the detector 103 detects X-rays applied from the X-ray tube of the X-ray source 102 and passing through the subject, the data collection unit 106 collects thus detected data to acquire a two-dimensional X-ray radiographic image. The X-ray radiographic image is transmitted from the data collection unit 106 to the data processor 109. Furthermore, the driver 105 changes the angle or the direction, and performs the same imaging process, resulting in that two X-ray radiographic images are acquired in total, including the result of the previous processing.

In step S201, the X-ray imaging apparatus 101 takes a plurality of two-dimensional images at different imaging angles. However, imaging is not necessarily required for acquiring an image. For example, the data processor 109 may further be configured to acquire from a predetermined database, or the like, a plurality of two-dimensional images taken at different imaging angles by another radiographic imaging apparatus.

Next, in step S202, the three-dimensional image capturing part 112 acquires a given three-dimensional image from the medical image server 110, and on the basis of this three-dimensional image, the calculated projection image generator 113 generates a two-dimensional calculated projection image. In step S203, the image alignment part 114 aligns the two-dimensional X-ray radiographic image acquired by the X-ray imaging apparatus 101 with the calculated projection image generated by the calculated projection image generator 113, and in next step S204, the characteristic region extractor 115 extracts the characteristic region in the X-ray radiographic image.

In next step S205, the deformation amount calculation and correction part 116 calculates a deformation amount of the subject, from the X-ray radiographic image and the calculated projection image. Processing related to the calculation of the deformation amount will be described later. In step S206, by using the deformation amount of the subject calculated by the deformation amount calculation and correction part 116 in step S205, and the characteristic region in the X-ray radiographic image extracted by the characteristic region extractor 115 in step S204, the position of the characteristic region in the X-ray radiographic image is corrected.

In the next step S207, the three-dimensional position calculator 117 calculates a three-dimensional position of the characteristic region in the X-ray radiographic image, the characteristic region having been extracted in the X-ray radiographic image and its position having been corrected based on the deformation amount. Subsequently, in step S208, a line connecting the three-dimensional position of the characteristic region in the X-ray radiographic image obtained in step S207 with the three-dimensional position of the X-ray source (see FIG. 7). When there is more than one characteristic region, a line connecting the three-dimensional position of the characteristic region in the X-ray radiographic image with the three-dimensional position of the X-ray source is obtained as to each of the characteristic regions.

In the present embodiment, in step S201, two X-ray radiographic images are obtained, and thus each processing in steps S202 to S208 is performed as to each of the X-ray radiographic images. Therefore, for one characteristic region, two lines are obtained, each connecting the three-dimensional position of the characteristic region in the X-ray radiographic image, with the three-dimensional position of the X-ray source. Therefore, when there are acquired a plurality of X-ray radiographic images, the number of the lines corresponding to the number of shots, should be obtained.

In step S209, the three-dimensional position calculator 117 calculates the three-dimensional position of the characteristic region, on the basis of the positional relationship between the two lines for the characteristic region obtained in step S208. In the next step S210, the anatomical structure position correction part 118 corrects the three-dimensional position of the characteristic region obtained in step S209, on the basis of the anatomical structure information of the subject, acquired from the medical image server 110 (see FIG. 8).

Then, in the next step S211, the position mapping part 119 superimposes the three-dimensional position of the characteristic region on the three-dimensional image, and delivers thus superimposed image data to the display unit 10 and to the memory unit 108. In step S212, the three-dimensional image on which the three-dimensional position of the characteristic region is superimposed, acquired from the three-dimensional position mapping part 119, is displayed on the display unit 108 (see FIG. 9), along with stored in the memory unit 108.

Subsequently, with reference to the flowcharts shown in FIGS. 11 and 12, there will be described a processing performed by the deformation amount calculation and correction part 116 for correcting the deformation that occurs on the subject, including the deformation due to body motion, and the deformation due to insertion of the treatment instrument into the body.

(Correction of Deformation Due to Body Motion)

Figure 11:
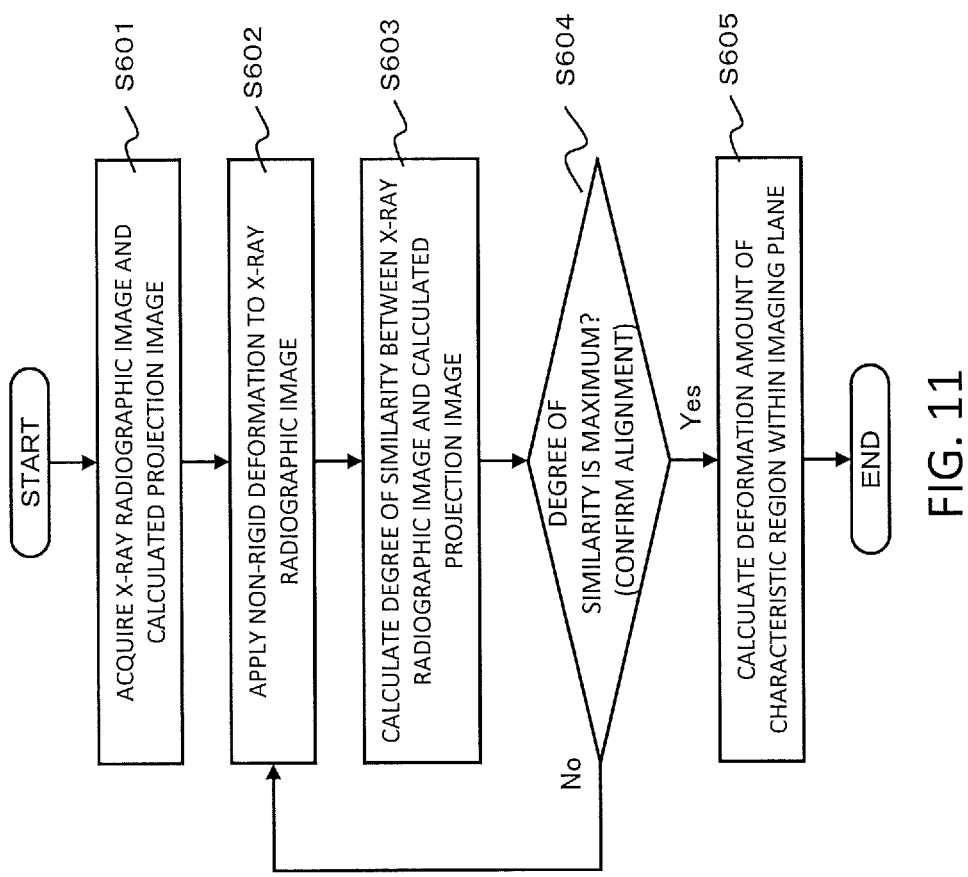
FIG. 11 is a flowchart showing a processing for correcting deformation due to body motion, in the deformation amount calculation and correction part of the X-ray imaging apparatus according to an embodiment of the present invention.

FIG. 11 is a flowchart showing the processing for correcting the deformation caused by body motion, according to the deformation amount calculation and correction part 116. In step S601, the non-rigid deformation part 501 acquires X-ray projected image aligned in step S204 of FIG. 10, and in step S602, subjects the X-ray radiographic image to non-rigid deformation. In the next step S603, the image comparator 502 compares the X-ray radiographic image after applying the non-rigid deformation by the non-rigid deformation part 501, with the calculated projection image of a rigid area, and then calculates a degree of similarity therebetween.

In step S604, the deformation parameter calculator 503 calculates a non-rigid deformation parameter on the basis of the degree of similarity calculated in the image comparator 502. The processing in step S604 determines whether the degree of similarity calculated in step S603 is maximum or not, and if not, the processing is repeated after returning to step S602. If the degree of similarity is a maximum, a parameter that maximizes a value indicating the degree of similarity (or minimizes the value indicating a degree of difference) is calculated as the non-rigid deformation parameter, and then processing goes to step S605.

In step S605, the in-imaging plane position correction part 504 calculates deformation displacement, representing how much has moved the position of the characteristic region in the two-dimensional image, on the basis of the non-rigid deformation parameter.

(Correction of Deformation Caused by Inserting Treatment Instrument into Body)

Figure 12:
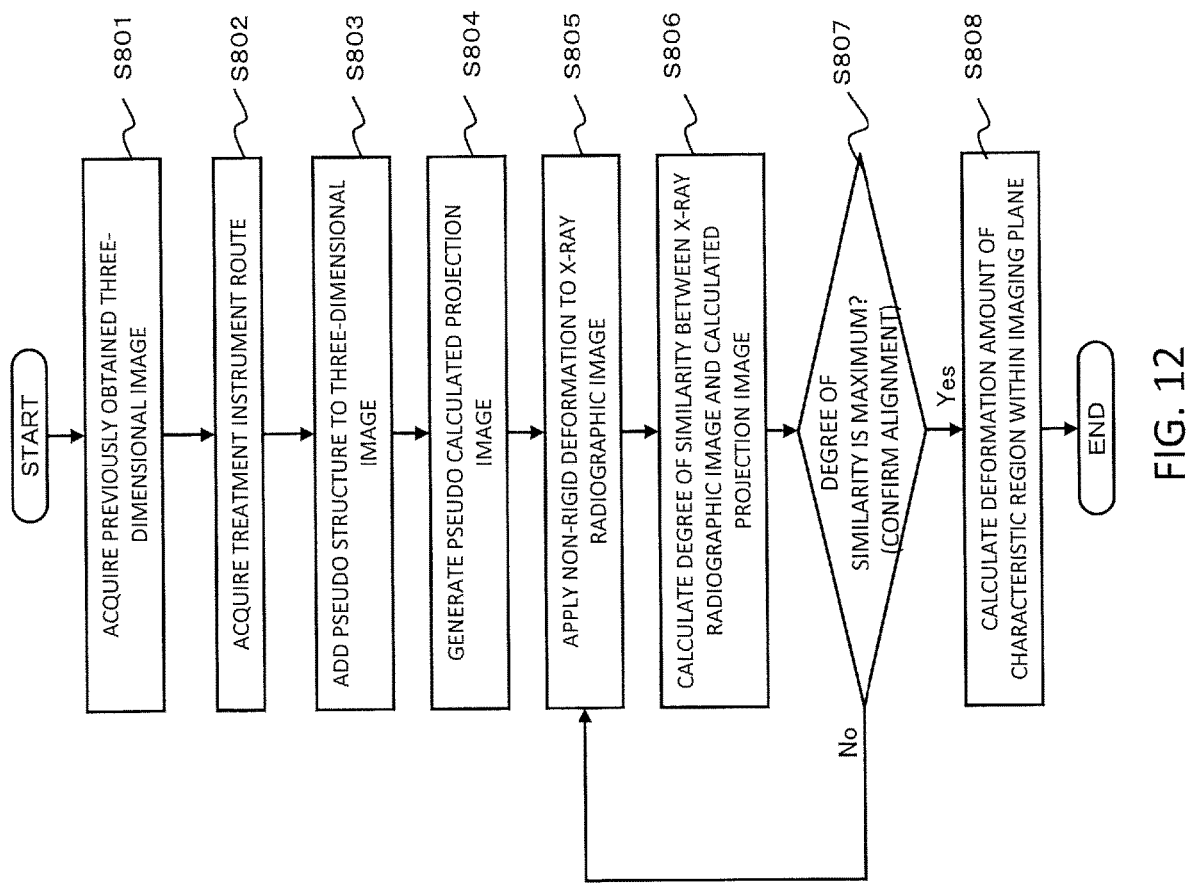
FIG. 12 is a flowchart showing a processing for correcting deformation due to insertion of the treatment instrument into a body, in the deformation amount calculation and correction part of the X-ray imaging apparatus according to an embodiment of the present invention.

FIG. 12 is a flowchart showing a processing according to the deformation amount calculation and correction part 116, for correcting deformation caused by inserting a treatment instrument into a body. The pseudo structure adder 505 acquires in step S801, the three-dimensional image having been obtained from the medical image server 110 by the three-dimensional image capturing part 112, and further acquires a treatment instrument route in step S802 (step S802).

In step S803, the pseudo structure adder 505 adds the treatment instrument route as a pseudo structure, to the three-dimensional image. Next, in step S804, the calculated projection image generator 113 generates a pseudo calculated projection image for the three-dimensional image to which the pseudo structure has been added by the pseudo structure adder 505. Generation of the pseudo calculated projection image from the three-dimensional image with the pseudo structure added, allows representation of a pseudo projection image of the treatment instrument, generated from the treatment instrument route, which is not represented in the three-dimensional image with no pseudo structure added.

In next step S805, the non-rigid deformation part 501 applies non-rigid deformation to the X-ray radiographic image, and in step S806, the image comparator 502 compares the X-ray radiographic image with the pseudo calculated projection image to which the pseudo structure is added, and calculates a degree of similarity therebetween.

In step S807, the deformation parameter calculator 503 calculates the non-rigid deformation parameter, on the basis of the degree of similarity calculated by the image comparator 502 in step S806. In the processing in step S807, it is determined whether the degree of similarity calculated in step S807 is maximum or not, and if not, the processing is repeated after returning to step S805. If the degree of similarity is a maximum, a parameter that maximizes a value indicating the degree of similarity (or minimizes the value indicating a degree of difference) is calculated as the non-rigid deformation parameter, and the processing goes to step S808.

In step S807, since the X-ray projected image is compared with the pseudo calculated projection image to which the pseudo structure is added, it is possible to obtain the non-rigid deformation parameter that considers not only the body motion but also the deformation in the subject due to insertion of the treatment instrument. In the next step S808, the in-imaging plane position correction part 504 uses the non-rigid deformation parameter calculated in S807 to calculate the deformation amount within the imaging plane. As described above, since the deformation of the subject is computed, with the use of the image to which the treatment instrument route is previously added as the pseudo structure, it is possible to correct the deformation of the subject, due to the insertion of the treatment instrument, in addition to the body motion.

According to the present embodiment as described so far, the three-dimensional position of the treatment instrument is detected accurately, and displayed on the image with a high degree of precision. In other words, in the present embodiment, the X-ray radiographic image and the three-dimensional image such as a CT image acquired in advance are used to detect the three-dimensional position of the treatment instrument. In particular, the position of the treatment instrument identified in the X-ray radiographic image, caused by internal body deformation of the subject due to not only body motion such as respiration and heart beating, but also insertion of the treatment instrument, is compared with the three-dimensional image acquired in advance, and then corrected. Therefore, the three-dimensional position of the treatment instrument can be detected accurately, and represented in the image, and this image can be displayed.

In addition, on the basis of the three-dimensional image, for example, the information regarding the insertion route of the treatment instrument is acquired, represented, and displayed, and this allows a user to identify the position of the treatment instrument and to easily ensure the insertion route.

A part or all of the data processor 109 may be configured as a system incorporating a CPU (central processing unit), a memory, and a main storage, and functions of components of the data processor 109 are implementable by the CPU that loads and executes programs stored in the storage in advance. Furthermore, a part or all of the functions may be configured by hardware such as ASIC (Application Specific Integrated Circuit) and FPGA (Field Programmable Gate Array).

DESCRIPTION OF SYMBOLS

101 . . . X-ray imaging apparatus, 102 . . . X-ray source, 103 . . . detector, 104 . . . device controller, 105 . . . driver, 106 . . . data collection unit, 107 . . . display unit, 108 . . . memory unit, 109 . . . data processor, 110 . . . medical image server, 111 . . . image processing system, 112 . . . three-dimensional image (anatomical structure/treatment instrument route) capturing part, 113 . . . calculated projection image generator, 114 . . . image alignment part, 115 . . . characteristic region extractor, 116 . . . deformation amount calculation and correction part, 117 . . . three-dimensional position calculator, 118 . . . anatomical structure position correction part, 119 . . . position mapping part, 501 . . . non-rigid deformation part, 502 . . . image comparator, 503 . . . deformation parameter calculator, 504 . . . in-imaging plane position correction part, 505 . . . pseudo structure adder

What is claimed is:

1. A radiographic imaging apparatus comprising,
an imager configured to take a plurality of two-dimensional pickup images at different imaging angles, by moving positions of a radiation source and a detector,
an image capturing part configured to acquire a three-dimensional image of a processing target imaged in advance,
a calculated projection image generator configured to generate two-dimensional calculated projection images from the three-dimensional image, respectively in association with the two-dimensional pickup images, on the basis of the three-dimensional image and the positions of the radiation source and the detector used for taking each of the two-dimensional pickup images,
a characteristic region extractor configured to extract a characteristic region indicating a treatment instrument represented in each of the two-dimensional pickup images,
an image alignment part configured to align each of the two-dimensional pickup images, with each of the calculated projection images respectively associated with the two-dimensional pickup images,
a deformation amount calculation and correction part configured to calculate a deformation amount of the processing target in each of the two-dimensional pickup images, by comparing each of the two-dimensional pickup images with each of the calculated projection images respectively associated with the two-dimensional pickup images, and to correct a position of the characteristic region based on the deformation amount,
a three-dimensional position calculator configured to calculate a three-dimensional position of the characteristic region, from the position of the characteristic region corrected in each of the two-dimensional pickup images, and the positions of the radiation source and the detector used for taking each of the two-dimensional pickup images, an anatomical structure position correction part configured to correct the three-dimensional position of the characteristic region based on anatomical structure information of the processing target acquired from the three-dimensional image, and a position mapping part configured to superimpose the three-dimensional position of the characteristic region corrected by the anatomical structure correction part, on the three-dimensional image, and to display the three-dimensional image on which the corrected three-dimensional position of the characteristic region is superimposed.

2. The radiographic imaging apparatus according to claim 1, wherein, the position mapping part superimposes on the three-dimensional image, the three-dimensional position of the characteristic region calculated by the three-dimensional position calculator, together with the corrected three-dimensional position of the characteristic region.

3. The radiographic imaging apparatus according to claim 1, wherein, the deformation amount calculation and correction part comprises, a non-rigid deformation part configured to apply non-rigid deformation to the two-dimensional pickup image, an image comparator configured to compare the two-dimensional pickup image after the non-rigid deformation is applied, with the calculated projection image to calculate a degree is similarity, a deformation parameter calculator configured to calculate a parameter that maximizes the degree of similarity as a non-rigid deformation parameter, and an in-imaging plane position correction part configured to calculate a deformation amount of the characteristic region in the two-dimensional pickup image on the basis of the deformation parameter, to correct the position of the characteristic region.

4. The radiographic imaging apparatus according to claim 2, wherein, the deformation amount calculation and correction part comprises, a non-rigid deformation part configured to apply non-rigid deformation to the two-dimensional pickup image, an image comparator configured to compare the two-dimensional pickup image after the non-rigid deformation is applied, with the calculated projection image to calculate a degree is similarity, a deformation parameter calculator configured to calculate a parameter that maximizes the degree of similarity as a non-rigid deformation parameter, and an in-imaging plane position correction part configured to calculate a deformation amount of the characteristic region in the two-dimensional pickup image on the basis of the deformation parameter, to correct the position of the characteristic region.

5. The radiographic imaging apparatus according to claim 3, wherein, the deformation amount calculation and correction part further comprises, a pseudo structure adder configured to superimpose a pseudo structure on the three-dimensional image, the pseudo structure representing a shape on the basis of an internal structure of the processing target.

6. The radiographic imaging apparatus according to claim 4, wherein, the deformation amount calculation and correction part further comprises, a pseudo structure adder configured to superimpose a pseudo structure on the three-dimensional image, the pseudo structure representing a shape on the basis of an internal structure of the processing target.

7. An image processing method comprising, an image capturing step for acquiring a plurality of two-dimensional pickup images of a processing target, taken at different imaging angles by changing positions of a radiation source and a detector, and a three-dimensional image of the processing target imaged in advance, a calculated projection image generating step for generating two-dimensional calculated projection images from the three-dimensional image, respectively in association with the two-dimensional pickup images, on the basis of the three-dimensional image and the positions of the radiation source and the detector used for taking each of the two-dimensional pickup images, a characteristic region extracting step for extracting a characteristic region indicating a treatment instrument represented in each of the two-dimensional pickup images, an image aligning step for aligning each of the two-dimensional pickup images, with each of the calculated projection images respectively associated with the two-dimensional pickup images, a deformation amount calculating and correcting step for calculating a deformation amount of the processing target in the two-dimensional pickup image, by comparing each of the two-dimensional pickup images with each of the calculated projection images respectively associated with the two-dimensional pickup images, and for correcting a position of the characteristic region based on the deformation amount, a three-dimensional position calculating step for calculating a three-dimensional position of the characteristic region, from the position of the characteristic region corrected in each of the two-dimensional pickup images and the positions of the radiation source and the detector used for taking each of the two-dimensional pickup images, an anatomical structure position correcting step for correcting the three-dimensional position of the characteristic region based on anatomical structure information of the processing target acquired from the three-dimensional image, and a position mapping step for superimposing the three-dimensional position of the characteristic region corrected by the anatomical structure correcting step, on the three-dimensional image, and for displaying the three-dimensional image on which thus corrected three-dimensional position of the characteristic region is superimposed.

8. A non-transitory computer readable medium storing thereon an image processing program causing a computer to execute, an image capturing step for acquiring a plurality of two-dimensional pickup images of a processing target, taken at different imaging angles by changing positions of a radiation source and a detector, and a three-dimensional image of the processing target imaged in advance, a calculated projection image generating step for generating two-dimensional calculated projection images from the three-dimensional image, respectively in association with the two-dimensional pickup images, on the basis of the three-dimensional image and the positions of the radiation source and the detector used for taking each of the two-dimensional pickup images, a characteristic region extracting step for extracting a characteristic region indicating a treatment instrument represented in each of the two-dimensional pickup images, an image aligning step for aligning each of the two-dimensional pickup images, with each of the calculated projection images respectively associated with the two-dimensional pickup images, a deformation amount calculating and correcting step for calculating a deformation amount of the processing target in the two-dimensional pickup image, by comparing each of the two-dimensional pickup images with each of the calculated projection images respectively associated with the two-dimensional pickup images, and for correcting a position of the characteristic region based on the deformation amount, a three-dimensional position calculating step for calculating a three-dimensional position of the characteristic region, from the position of the characteristic region corrected in each of the two-dimensional pickup images and the positions of the radiation source and the detector used for taking each of the two-dimensional pickup images, an anatomical structure position correcting step for correcting the three-dimensional position of the characteristic region based on anatomical structure information of the processing target acquired from the three-dimensional image, and a position mapping step for superimposing the three-dimensional position of the characteristic region corrected by the anatomical structure correcting step, on the three-dimensional image, and for displaying the three-dimensional image on which thus corrected three-dimensional position of the characteristic region is superimposed.

* * * * *